United States Patent
Rebstock et al.

[11] Patent Number: 5,877,675
[45] Date of Patent: Mar. 2, 1999

[54] WIRELESS HEALTHCARE COMMUNICATION SYSTEM

[75] Inventors: Janice I. Rebstock; T. Paul Rast, both of Gainesville, Fla.

[73] Assignee: Jansys, Inc., Gainesville, Fla.

[21] Appl. No.: 705,307

[22] Filed: Aug. 29, 1996

[51] Int. Cl.[6] .................................................. G08B 7/00
[52] U.S. Cl. ................ 340/286.07; 340/539; 340/573.1; 340/825.08; 340/825.49; 128/903; 128/904; 455/66; 455/100; 455/524
[58] Field of Search .......................... 340/286.06, 286.07, 340/539, 573.1, 825.08, 825.49, 825.36; 128/903, 904; 455/66, 90, 517, 524, 100

[56] References Cited

U.S. PATENT DOCUMENTS

| | | | |
|---|---|---|---|
| 3,572,316 | 3/1971 | Vogelman et al. | 128/903 |
| 3,646,606 | 2/1972 | Buxton et al. | 128/903 |
| 3,972,320 | 8/1976 | Kalman | 340/573 |
| 4,194,179 | 3/1980 | Malinouskas | 128/903 |
| 4,321,933 | 3/1982 | Baessler | 128/903 |
| 4,503,862 | 3/1985 | Baessler | 128/903 |
| 4,573,475 | 3/1986 | Dukes et al. | 128/903 |
| 4,686,998 | 8/1987 | Robbins | 128/903 |
| 4,847,818 | 7/1989 | Olsen | 379/428 |
| 4,947,152 | 8/1990 | Hodges | 340/573 |
| 5,223,816 | 6/1993 | Levinson et al. | 340/539 |
| 5,335,664 | 8/1994 | Nagashima | 128/903 |
| 5,396,224 | 3/1995 | Dukes et al. | 340/573 |
| 5,534,851 | 7/1996 | Russek | 340/573 |
| 5,537,459 | 7/1996 | Price et al. | 340/286.07 |
| 5,561,412 | 10/1996 | Novak et al. | 340/286.07 |
| 5,652,570 | 7/1997 | Lepkofker et al. | 340/573 |

OTHER PUBLICATIONS

Dukane ProCare 6000 Product Brochures, 1995.
Executone Infostar/ILS Product Brochure, 1994.

Primary Examiner—Daniel J. Wu

[57] ABSTRACT

A portable, three-way wireless communication system provides a patient with a direct link to a caregiver, as well as a central facility such as a nurse's station. The system is comprised of a patient unit, a caregiver unit and a central station. The patient unit is designed to be small and portable, and can be worn on the patient's wrist or the like. The unit permits a patient to send a request for assistance directly to an assigned caregiver, and provides for two-way voice communications between the patient and the caregiver. The unit stores information associated with the patient, such as identification, medications, attending physician, and the like. The caregiver unit is also portable, and provides two-way voice communications with patients and other caregivers. The unit displays information about each patient to whom the caregiver is assigned. The central station functions as a backup, in the event that a caregiver is not able to timely respond to a call from a patient. In addition, it stores more detailed information regarding patients, which can be accessed by the caregiver via their individual units. It also functions as a management quality control facility, by recording all transmissions that take place via any unit in the communication system, and providing reports that indicate the calls for assistance, times of the calls, times of the responses by caregivers, and the like. The system functions to indicate the locations of respective patients by means of a distributed network of sensors throughout an area of interest, such as the buildings and grounds of a healthcare facility.

17 Claims, 4 Drawing Sheets

5,877,675

WIRELESS HEALTHCARE COMMUNICATION SYSTEM

FIELD OF THE INVENTION

The present invention is directed to systems for providing communications between patients and caregivers in healthcare facilities, such as hospitals, nursing homes and the like, and more particularly to communication systems which are designed for use with patients who are not confined to their beds, or another single location.

BACKGROUND OF THE INVENTION

Most healthcare facilities employ some type of system which permits a patient who is confined to a bed to communicate with a caregiver who is located at a central facility, e.g. a nurse's station. An exemplary system employs a call button that is located on the end of an extension cord, and which can be clipped to a bedsheet or wrapped around a bedrail. When a patient requires assistance, the call button is pressed, which sends a signal to the central facility. In addition, it may cause a light or other indicator to be actuated immediately outside the patient's room, to thereby alert a caregiver in the vicinity of the room to the fact that the patient needs assistance. If no caregiver happens to be in the immediate vicinity, the call can be acknowledged by a person at the central facility, for example by means of a two-way intercom. This person can then notify the patient's caregiver, who can attend to the patient's needs.

Communication systems of this type have certain limitations associated with them. First and foremost is the fact that they require the patient to be near his or her bed to call for needed assistance. Although useful where patients are confined to their beds, they are less practical for patients who are free to move about. This concern is particularly relevant in nursing homes where the patients, or residents, are encouraged by governmental regulations to attend various activities outside of their rooms, and hence are frequently away from their beds and the call buttons.

As another concern, the typical cord length does not facilitate access to the button even at short distances from the bed. Thus, a patient who has fallen by the bedside or is in another area of the facility is not able to use the system to call for help.

As another consideration, the typical call button type of system is designed to be staff oriented. As such, it does not provide direct communication between the patient and the caregiver, whose duties may require him or her to be in different areas of the facility, and hence not always near the patient. Current systems require the caregiver to be in the vicinity of the patient's room, so that the visual indicator can be observed. Otherwise, it is necessary for the person at the central facility, who receives the call, to locate and notify the caregiver, which may require an inordinate amount of unnecessary waiting time on the part of the patient.

It is desirable, therefore, to provide a healthcare communication system that facilitates direct communication between a patient and his or her assigned caregiver. It is further desirable to provide such a system which is fully portable, and thereby not restricted to use only when the patient is in or near a bed.

SUMMARY OF THE INVENTION

In accordance with the present invention, these objectives are achieved by a portable, three-way wireless communication system that provides a patient with a direct link to a caregiver, as well as a central facility such as a nurse's station. The system is comprised of three main components, a patient unit, a caregiver unit and a central station. The patient unit is designed to be small and portable, and can be worn on the patient's wrist or the like. The unit permits a patient to send a request for assistance directly to an assigned caregiver, and also provides for two-way voice communications between the patient and the caregiver. In addition, the unit can store information associated with the patient, such as identification, medications, attending physician, and the like.

The caregiver unit is also portable, so that it can be carried by the caregiver and provide instant two-way voice communications with patients and other caregivers. The unit displays information about each patient to whom the caregiver is assigned. In response to a call from a given patient, the caregiver unit displays all information relevant to that patient.

The central station functions as a backup, in the event that a caregiver is not able to timely respond to a call from a patient. In addition, it provides the capability to store more detailed information regarding patients, which can be accessed by the caregiver via their individual units. It also functions as a management quality control facility, by recording all transmissions that take place via any unit in the communication system, and providing reports that indicate the calls for assistance, times of the calls, times of the responses by caregivers, and the like.

As a further feature, the communication system of the present invention functions to indicate the locations of respective patients. By means of a distributed network of sensors throughout an area of interest, such as the buildings and grounds of a healthcare facility, the whereabouts of patients can be monitored at all times. As a result, patients who may have fallen or become trapped in a room can be readily located and provided with assistance.

The foregoing features of the invention, as well as the advantages provided thereby, are explained in greater detail hereinafter with reference to a preferred embodiment illustrated in the accompanying drawings.

DETAILED DESCRIPTION

To facilitate an understanding of the present invention, it is described hereinafter with particular reference to its implementation in a healthcare facility such as a nursing home, in which it is anticipated that patients, or residents, are able to move freely about the facility, rather than being confined to a single location. It will be appreciated, however, that the practical applications of the invention are not limited to this particular environment. Rather, the invention will find utility in any situation in which it is desirable to provide communication between persons who require assistance and those who provide the assistance to them.

Figure 1:
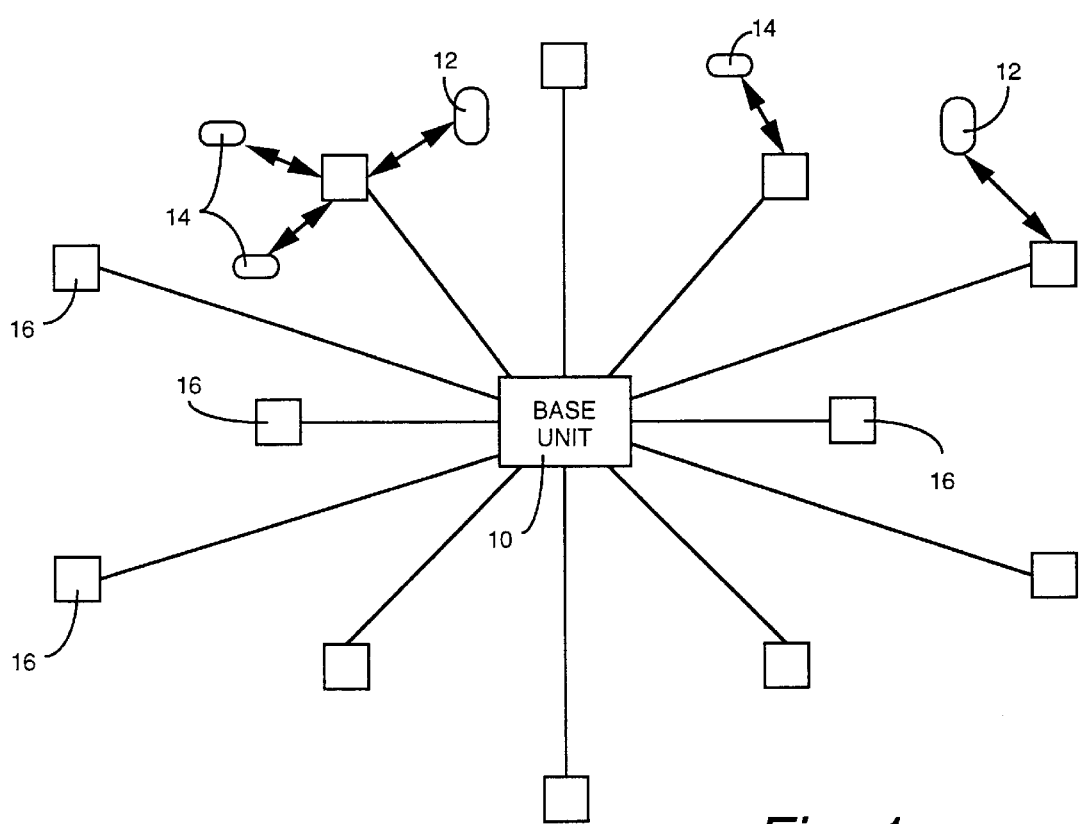
FIG. 1 is a block diagram illustrating a general overview of a communication system in accordance with the present invention.

FIG. 1 is a general overview of a communication system which embodies the principles of the present invention. The system is comprised of three main components, namely a base unit 10, a plurality of caregiver units 12 and a plurality of patient units 14. Each of these units functions as a two-way communication device. To facilitate direct communications between individual units, each is identified with a unique code and all communications to a particular unit are addressed with its code. Both the caregiver units 12 and the patient units 14 are designed to be portable, and communicate with each other, as well as with the base unit 10, by means of radiowave communications. Distributed throughout an area of interest, such as the grounds and buildings of the healthcare facility, are a number of repeater units 16. These repeater units are combined transmitter and receivers that function to relay communications between the base unit 10, the caregiver units 12 and the patient units 14. In one embodiment of the invention, the base unit communicates with the repeaters by means of radiowave communications. However, since the base unit and the repeaters are stationary, it will be appreciated that they can be connected to each other via fixed communication media, such as copper wires or optical cables.

The number and location of the repeater units 16 is determined with two principle objectives. First, since the patient units 14 are preferably small in size, they employ small batteries and therefore have low transmission power, to preserve battery life. Accordingly, the repeaters are spaced at distances from one another which ensure that the low-power signal from a patient unit can be reliably received at least at one repeater unit from any location within a desired area of coverage, such as the buildings and grounds of a healthcare facility.

In addition to relaying communications between the patient units, the caregiver units and the base unit, the repeaters can also function to provide information regarding the location of each patient. For example, each patient unit can be provided with a unique identification code. On a regular basis, each patient unit is polled by the base station. For example, the base station may cause each repeater to send a signal which requires a particular patient unit to respond, and thereby identify itself. When a response is received from the particular patient unit being polled, it is identified as being in the location of the repeater which receives the strongest signal from it. In such a case, the repeaters should be adequate in number, and sufficiently close to one another, to provide the desired degree of resolution regarding the locations of the patients. For example, in outdoor areas, fine resolution may not be necessary, in which case a few repeaters can be used. However, within a building, to differentiate between different rooms, it may be desirable to put a separate repeater in each room.

Figure 2:
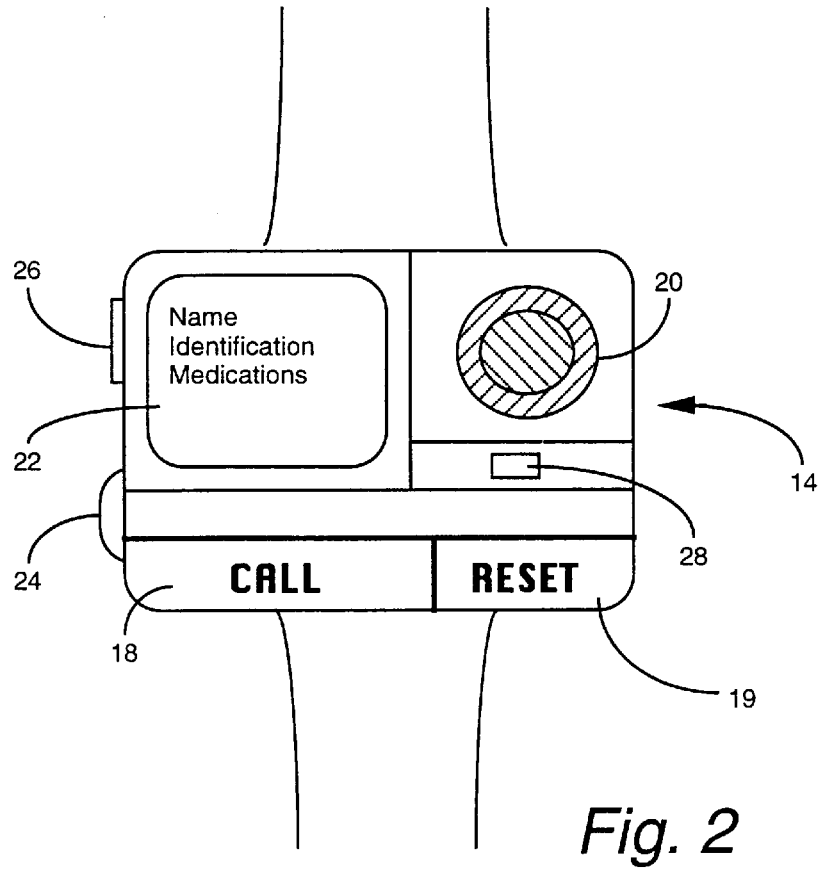
FIG. 2 is a plan view of a patient wrist unit.
Figure 3:
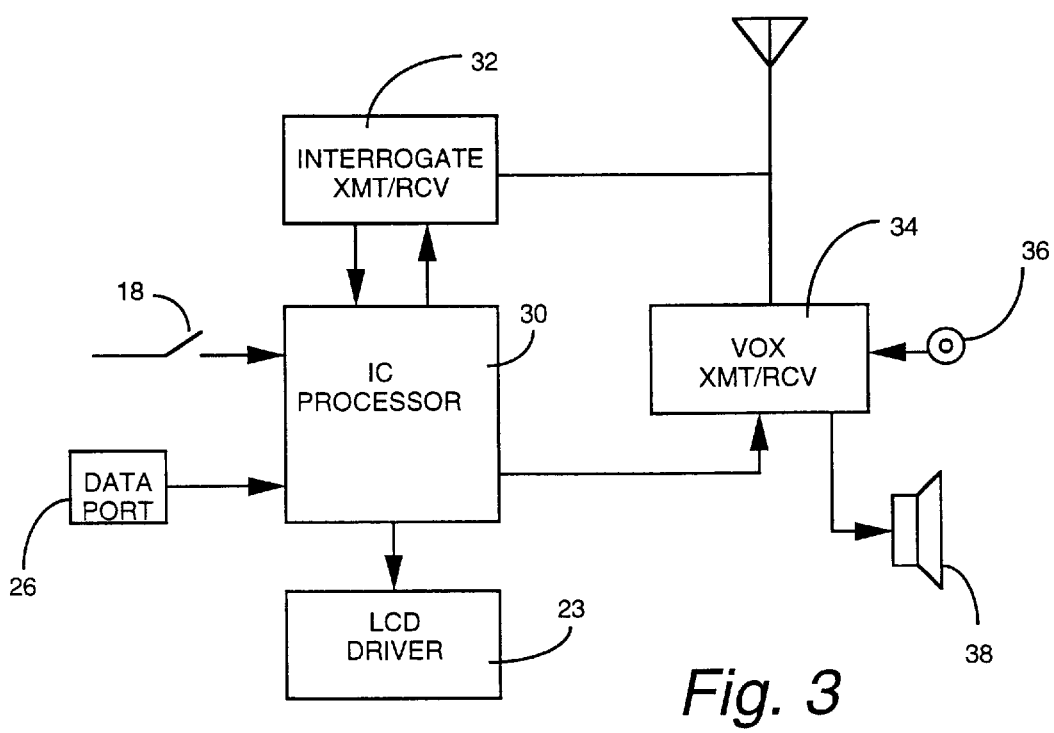
FIG. 3 is a schematic block diagram of the circuit for a patient unit.

FIG. 2 is an illustration of the patient unit 14, and FIG. 3 is a schematic block diagram of the unit. The patient unit 14 is preferably designed to be worn on the wrist of a patient, and to take the place of the conventional patient wristband or identification bracelet typically found in most hospitals and nursing homes. One of the principle functions of the patient unit is to initiate a call to a caregiver in the event that the patient needs assistance. For this purpose, the patient unit is provided with a relatively large call button 18 that can be easily actuated by patients, including those having limited motor functions. Preferably, the call button 18 is illuminated, so that it can be readily seen by the patient in dark environments. Further in this regard, the profile of the call button can be raised above the main surface of the patient unit, to provide tactile access.

Another function of the patient unit is to provide two-way voice communications between the patient and his or her assigned caregiver. For this purpose, the patient unit includes a microphone/speaker unit 20. Preferably, the microphone is voice activated, for greater convenience of the patients. To conserve power, and prevent unnecessary transmissions, the voice activation function can be enabled by the depression of the call button 18. Alternatively, the patient unit can have voice recognition capabilities, so that if the patient utters a particular keyword, such as "nurse" or "help", a call signal to the caregiver is initiated.

Another function of the patient unit 14 is to provide a limited amount of information pertaining to the patient. For this purpose, the unit is provided with an LCD display 22, via which information such as the patient's name and ID number, medications and allergies, attending physician, and other significant information can be displayed. A button 24 on the side of the unit is used to activate the display to provide this information. The unit also has a data port 26 via which the relevant information is downloaded. To facilitate maintenance and ensure continued communications, a battery charge indicator 28 is located on the front of the unit.

Referring to FIG. 3, the operation of the patient unit is controlled by a small integrated circuit microprocessor 30, which includes associated memory (not shown). Data is loaded into the memory via the data port 26. This data can include the name and identification of the patient, the relevant medication and allergy information, and any other significant medical history that may be desired. In addition, the unit is provided with a unique identification code, which can be loaded into its memory via the data port, or permanently stored therein at the time of manufacture. When the display button 24 is actuated, the processor 30 causes the relevant information to be displayed on the LCD unit 22, via an associated LCD driver circuit 23. If the amount of information to be displayed is greater than that which can be shown on the screen 22 at one time, the unit can be provided with a suitable scroll button or page toggle button (not shown).

In response to activation of the call button 18, the processor 30 actuates an interrogation transmit/receive unit 32. This unit causes a call signal to be transmitted, to alert a caregiver that the patient needs attention. The call signal which is transmitted by the interrogation unit is addressed with a unique code assigned to the caregiver unit of the particular person assigned to that patient, which is downloaded into the memory. In addition, the transmitted call signal is encoded with the patient's identification, which can be displayed to the caregiver (as described below) to provide an immediate indication of the person who needs assistance.

Preferably, the patient unit 14 continually transmits the call signal on a periodic basis, e.g., every minute, until the patient has received the requested attention. For this purpose, the unit can be provided with a reset button 19, which is actuated by the caretaker once he or she reaches the patient. Alternatively, the patient unit can transmit a call signal only when the call button 18 is actuated. In this case, actuation of the reset button can function to provide an indication that the caretaker has responded to the call, as described in detail hereinafter.

The interrogation unit 32 also functions to receive polling signals that are transmitted from the base unit 10 via the repeater 16. Each polling signal is encoded with the unique identification code of one of the patient units. When a patient unit receives a polling signal which contains its unique code, the processor 30 actuates the unit 32 to transmit a response signal. This response signal preferably includes the unique code of the patient unit, to thereby distinguish among multiple transmissions which may be occurring at the same time.

The patient unit includes a voice activated transmit/receive unit 34. As described previously, this unit can be enabled by the microprocessor 30, through actuation of the call button 18. When so enabled, input provided to a microphone 36 is transmitted to the repeater units, and communications from the base station and the caregiver units are reproduced via a speaker 38.

Figure 4:
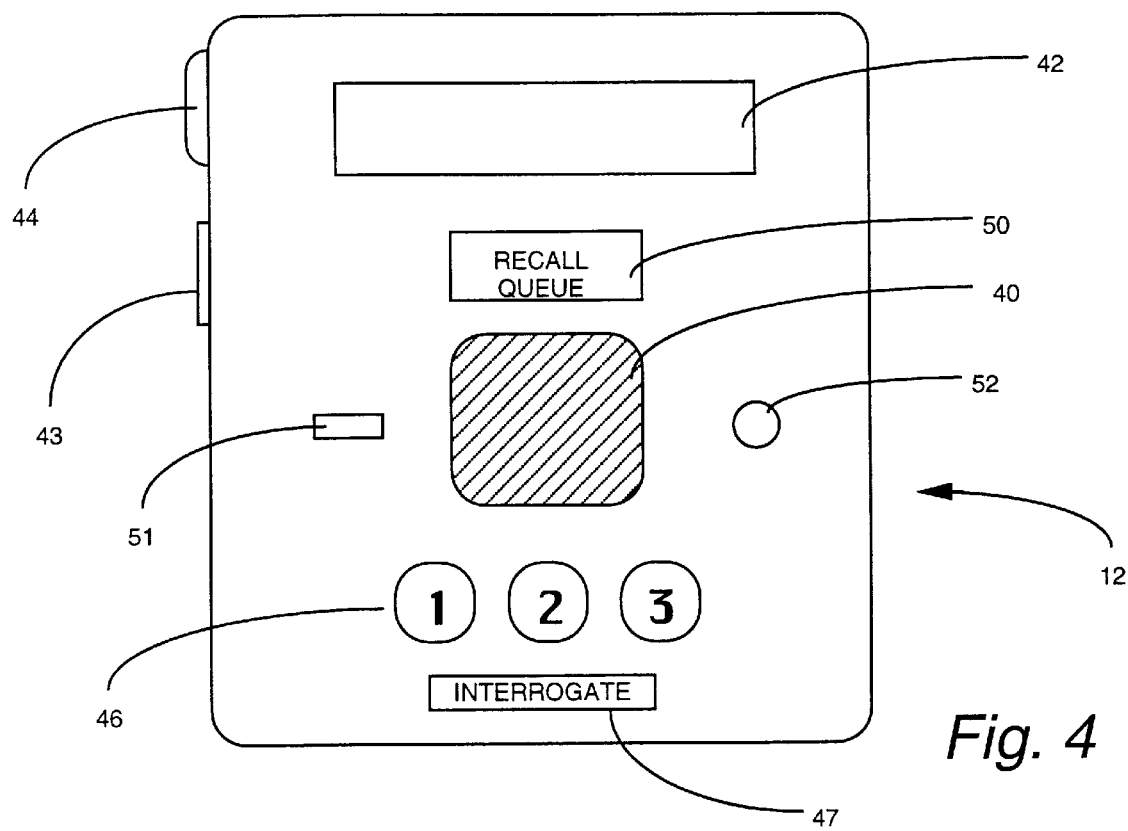
FIG. 4 is a plan view of a caregiver unit.
Figure 5:
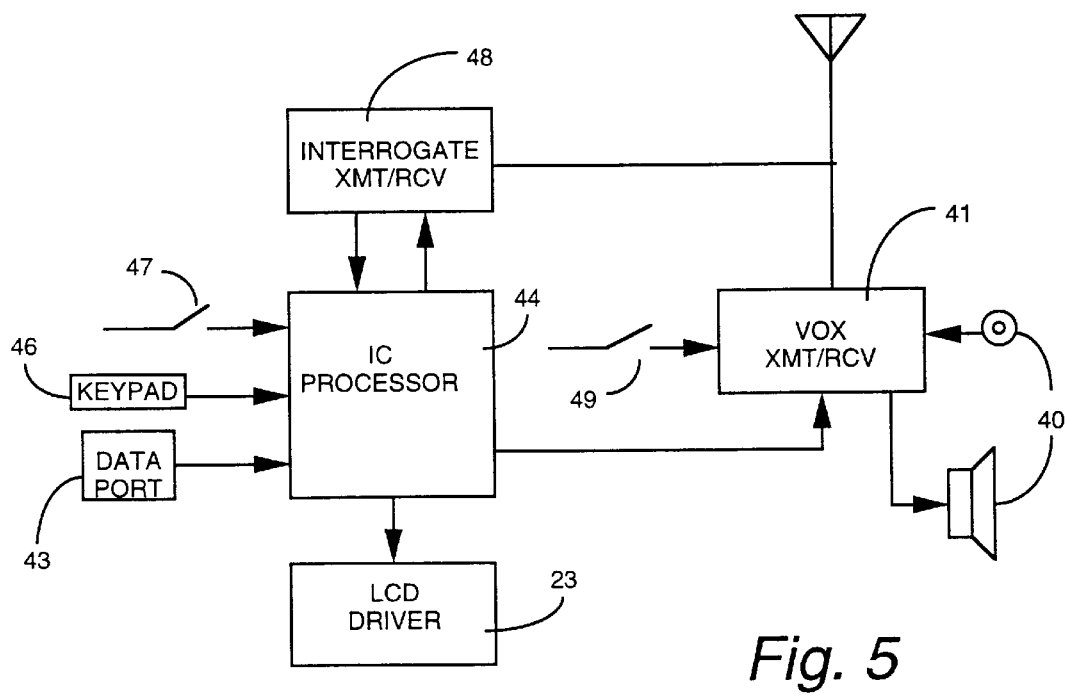
FIG. 5 is a schematic block diagram of the caregiver unit.

FIG. 4 is a plan view of the caregiver unit 12, and FIG. 5 is a schematic block diagram of the circuit for the caregiver unit. In many respects, the caregiver unit is similar to the patient unit, in terms of providing information to the caregiver and communications with the patients. Thus, the unit includes a combined speaker and microphone 40 connected to a voice activated transmit/receive unit 41. The caregiver unit also includes an LCD display 42 which displays relevant patient data that has been downloaded via a data port 43 and stored in memory associated with an IC processor 44. The processor 44 controls the display of data through an associated LCD driver 45.

Since each caregiver in a facility will likely have responsibility for several patients, the caregiver unit must be capable of individually communicating with each of those patients. To provide the caregiver with the ability to selectively address communications to individual patients, it is provided with a keypad 46, via which the caregiver can select a particular patient. Upon depression of the keys to enter a patient's identification, the relevant information pertaining to that patient can be displayed on the LCD unit 42. Thus, the caregiver can use the keypad to scroll through the data pertaining to each assigned patient. When the identification of a particular patient of interest is displayed, an interrogate button 47 can be actuated to send a signal to that particular patient. In response to actuation of this button, the IC processor 44 retrieves the unique code associated with the patient unit of interest, and forwards it to an interrogation transmit/receive unit 48, to cause it to send a signal addressed to the unit of interest. In response to receipt of this signal, the patient unit can generate an audible signal, to alert the patient that the caregiver desires to communicate with him or her. Once the patient responds, the caregiver can talk with the patient via the speaker/microphone 40. To activate the voice communication capabilities, a separate button 49 can be provided on the caregiver unit.

If desired, the keypad 46 can also be used to update patient information stored in the memory for the processor 44. The keypad can be employed as an alternative to the data port 46 for relatively minor changes, such as when an assigned patient transfers to a new room, or is discharged. In this case, the keypad will likely comprise more than the three exemplary keys illustrated in FIG. 4.

In some cases, the caretaker may receive two or more calls for assistance while attending to the needs of a particular patient. In such a situation, the calls are stored in the order in which they arrive at the caregiver unit. To display all calls which are currently pending, the caregiver unit is provided with a queue recall button 50. In response to actuation of this button, the pending calls for assistance are displayed on the LCD device 42 in order of initial receipt.

The caregiver unit 12 includes a low battery indicator 51, and an alert indicator 52. The alert indicator 52 can be constantly illuminated whenever a call for assistance is pending, to remind the caregiver of that fact in the event that the queue is not currently being displayed on the LCD device 42.

Figure 6:
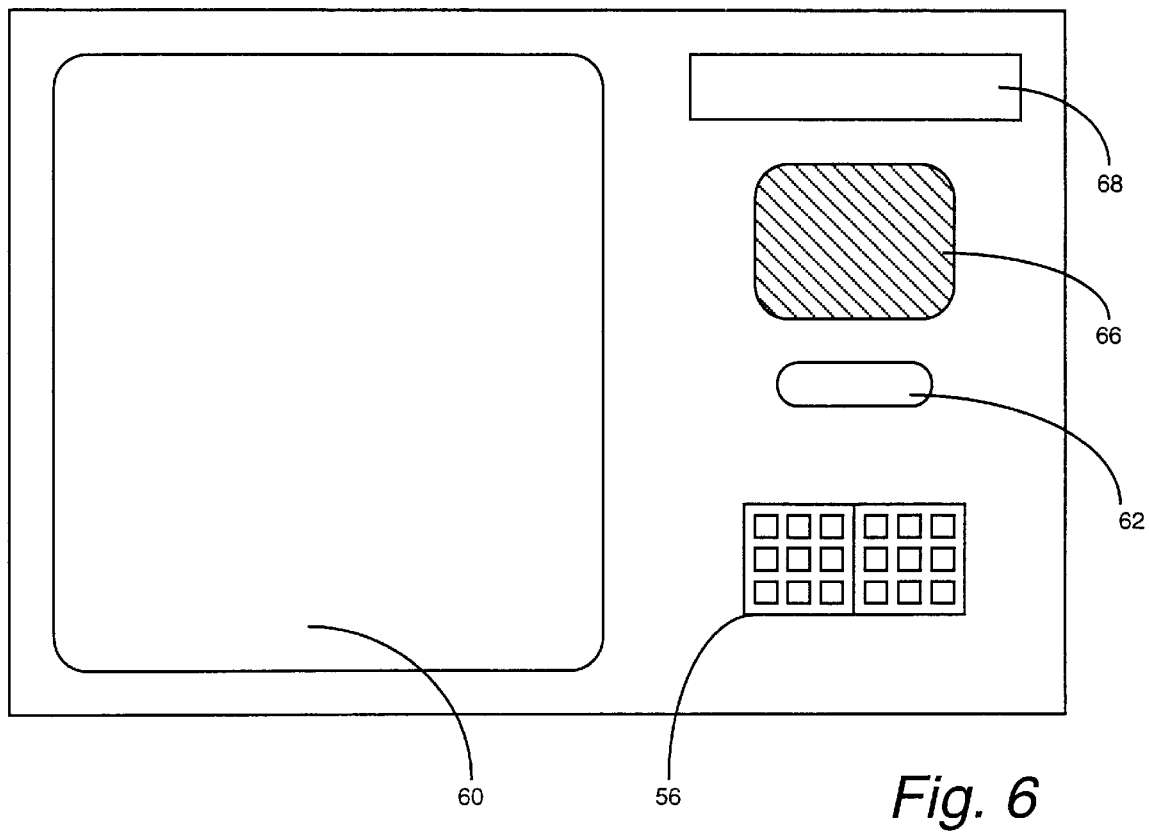
FIG. 6 is an illustration of a console for a base unit.
Figure 7:
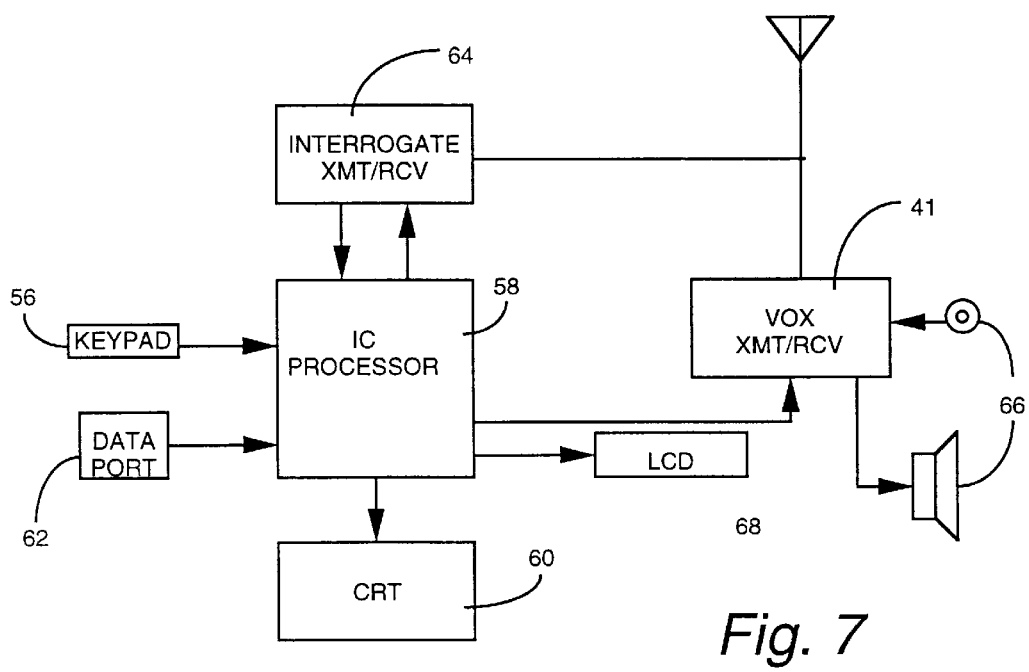
FIG. 7 is a schematic block diagram of the circuit for a base unit.

FIG. 6 is an illustration of a console at a base unit 10, and FIG. 7 is a schematic block diagram of the circuit for the base unit. The base unit primarily functions as a repository of all information relevant to the various patients, as well as a central station for coordinating the communications between the patients and the caregivers. Information about each patient is entered through a suitable keypad 56, and stored in a memory associated with an IC microprocessor 58. The data is displayed on a CRT display 60 on the console. For example, the organization and display of the data can be carried out through any suitable type of database application program.

At least some of the data which is entered into the base unit is also stored in each of the caregiver and patient units. For this purpose, therefore, the base unit is provided with a data port 62, which is connectible to the data ports on the individual patient units 14 and caregiver units 12. Once the base unit is connected to one of these other units, the data to be downloaded can be selected and displayed on the CRT 60, and then transferred to the individual unit.

The base unit functions to initiate polling requests to all of the patient units, to determine the locations of the respective patients. To this end, on a regular basis the microprocessor 58 retrieves the code associated with a particular patient unit, and provides it to an interrogation transmit/receive unit 64. In response, the interrogation unit 64 sends a signal to each of the repeaters 16, which transmit a polling request signal that is addressed to a particular one of the patient units. When the patient unit responds, as described previously, the received signal is forwarded to the base unit. Each repeater also indicates that strength of the received signal, when it forwards the response. Based upon the relative strengths received at each of the repeaters, the base unit determines the most likely location of the responding patient unit. For example, the patient unit can be considered to be within the vicinity of the repeater which received the strongest signal. This information can be displayed on the console 60 along with the other patient identification information, and stored in the database record associated with the patient.

The base unit functions as a backup communication station, in the event that a patient's request for assistance is not acknowledged by his or her assigned caregiver. When a call signal is sent from a patient unit 14, it is received at the base station as well as at the particular caregiver unit to which it is assigned. At the base station, a timer can be initiated by the microprocessor upon receipt of the call signal from the patient unit. When the assigned caregiver responds to the call, and depresses the reset button 19 on the patient's unit, that response is transmitted to the base unit. Upon receipt of the caregiver's response, the timer is stopped. However, if the caregiver does not respond within a predetermined period of time, an alert can be flashed on the CRT display and, if desired, an audible signal can be generated. In response thereto, a person located at the base station can communicate with the calling patient, via a speaker/microphone 66. When communications are being carried out with a particular individual, the identification and location of that individual is displayed on an LCD display unit 68.

Whenever a call is sent from any of the patient units, upon receipt thereof the base unit can retrieve the stored location of the patient and transmit it to the appropriate caregiver unit, where it can be displayed along with the patient identification.

The base unit 10 provides administrative monitoring and report capabilities. To this end, all calls for assistance which are initiated from any of the patient units 14, as well as responses transmitted from the caretaker units 12 and base unit 10, are recorded at the base unit, along with data such as the time of the transmission, the number of times a particular patient unit initiated a call, the location of the patient, and the elapsed time before a response was made. This data can be displayed and/or printed to provide quality control reports which enable management of the facility to assess the requirements, allocation and effectiveness of the caregiving operation.

From the foregoing, it can be seen that the present invention provides a communication system which facilitates direct communication between patients, assigned caregivers, and personnel at a central facility. Since the patient units and caregiver units are portable, direct communications between the two can take place regardless of the relative locations of the patients and the caregivers, thereby enabling prompt responses and reducing activity at the central nurses' station. Since all communications are monitored through the base unit, a response is always ensured even when an assigned caregiver is not capable of immediately responding. By continually monitoring the locations of the patients, the caregiver is always able to readily determine where assistance is needed, thereby reducing response time to critical events such as accidents and falls. Furthermore, by storing a limited amount of data in each of the patient units and caregiver units, critical information is readily available so that proper assistance can be provided in any situation.

It will appreciated by those of ordinary skill in the art that the present invention can be embodied in other specific forms without departing from the spirit or essential characteristics thereof. The presently disclosed embodiments are considered in all respects to be illustrative, and not restrictive. The scope of the invention is indicated by the appended claims, rather than the foregoing description, and all changes that come within the meaning and range of equivalents thereof are intended to be embraced therein.

What is claimed is:

1. A wireless communication system for healthcare facilities, comprising:
   a portable patient communication unit that is adapted to be worn on the body of a patient, said patient communication unit including (a) means for transmitting a signal which indicates a request for assistance, (b) means for conducting wireless two-way voice communication, and (c) a memory and display device for storing and displaying information about a patient which is useful to a caregiver in providing assistance to the patient;
   a portable caregiver communication unit that is adapted to be carried by a caregiver, said caregiver communication unit including (a) means for receiving assistance signals transmitted by the patient communication unit and alerting a caregiver of the receipt of such a signal, (b) means for conducting wireless two-way voice communications with the patient communication unit, and (c) means for storing and displaying information about individual patients;
   a base unit for monitoring and recording assistance signals transmitted from the patient communication unit and for conducting wireless two-way voice communications with each of said patient communication unit and said caregiver communication unit; and
   a plurality of transmit/receive units distributed throughout an area of interest for relaying assistance signals and two-way voice communications between each of said patient communication unit, said caregiver communication unit and said base unit, and for monitoring the location of said patient communication unit within said area of interest.

2. The wireless communication system of claim 1 wherein said patient communication unit is adapted to be worn on the wrist of the patient.

3. The wireless communication system of claim 1, wherein said caregiver unit includes a signaling device for acknowledging to the base unit that a caregiver has responded to a call from a patient unit, and said base unit includes a timer for generating a warning signal if a response from a caregiver unit is not received within a predetermined period of time after receipt of a call from a patient unit.

4. The wireless communication system of claim 1, wherein said base unit includes means for polling said patient communication unit via said transmit/receive units, and means for identifying the location of the patient communication unit based on responses received at said transmit/receive units.

5. The wireless communication system of claim 4, wherein the location of a patient communication unit is determined on the basis of the relative strengths of signals received at said transmit/receive units from a patient communication unit in response to a polling signal.

6. The wireless communication system of claim 1, wherein said base unit includes a memory storing information relating to the individual healthcare needs of a plurality of patients.

7. The wireless communication system of claim 6, further including a data communication port in each of said base unit and said caregiver communication units for connecting said caregiver communication units to said base unit to download information relating to the individual healthcare needs of patients from the memory in said base unit to the storing means in said caregiver communication units.

8. The wireless communication system of claim 7, further including a data communication port in each of said patient communication units for connecting said patient communication units to said base unit to download information relating to the individual healthcare needs of patients from the memory in said base unit to the memories in said patient communication units.

9. A patient communication unit for use in a wireless communication system for healthcare facilities, comprising:
   a housing that is adapted to be worn on the wrist of a patient;
   a manually actuated member on said housing for initiating a call for assistance;
   a processor within said housing that is responsive to actuation of said member for transmitting a signal which indicates a request for assistance, said signal being uniquely encoded to identify the patient communication unit;
   a memory associated with the processor for storing data relating to a patient;
   a display device on said housing for displaying data stored in said memory; and
   a wireless two-way voice communication device contained within said housing.

10. The patient communication unit of claim 9 wherein said communication device is voice-activated.

11. A wireless communication system for healthcare facilities, comprising:
   a) a plurality of patient units, each of which includes:
      means for conducting wireless voice communication, and
      means for transmitting a unique call signal independently of voice communications;
   b) a plurality of caregiver units, each of which is responsive to unique call signals from at least one associated patient unit for providing an alert indication, and each of which includes:
      a memory for storing prerecorded information pertaining to the individual healthcare of a plurality of patients,
      a display device for displaying said prerecorded information about patients,
      means for selectively retrieving information about individual patients for display on said display device, and
      means for initiating wireless voice communications with a patient unit associated with a patient whose information is displayed on said display device; and
   c) a base unit for receiving said unique call signals from said patient units and including:
      a memory storing said information with respect to a plurality of patients,
      means for conducting wireless voice communication with each of said patient units and said caregiver units; and
      means to download information relating to the individual healthcare needs of patients from the memory in said base unit to the memories in individual caregiver units, independently of said voice communications.

12. The system of claim 11 wherein each patient unit includes a memory for storing information pertaining to a patient, and a display device for displaying the stored information.

13. The system of claim 11 wherein said base unit automatically records data pertaining to each call signal transmitted from the patient units.

14. The system of claim 11 further including a communication network comprising a plurality of transmit/receive units distributed throughout an area, each of said transmit/receive units functioning to relay call signals and voice communications between said patient units, said caregiver units and said base unit.

15. The system of claim 14 further including means for determining the location of respective patient units within said area.

16. The system of claim 15 wherein said determining means includes means for individually polling each of said patient units, and means for identifying the location of a patient unit based upon responses to a polling signal received at said transmit/receive units.

17. The wireless communication system of claim 16, wherein said identifying means includes a plurality of receiver units dispersed throughout an area in which said patient units might be located, and the location of a patient unit is determined on the basis of the relative strength of signals received at said receiver units from a patient unit in response to a polling signal.

* * * * *